(12) United States Patent
Larson-Smith et al.

(10) Patent No.: US 9,429,533 B2
(45) Date of Patent: *Aug. 30, 2016

(54) DURABLE TRANSPARENT INTELLIGENT COATINGS FOR POLYMERIC TRANSPARENCIES

(71) Applicant: The Boeing Company, Chicago, IL (US)

(72) Inventors: Kjersta L. Larson-Smith, Seattle, WA (US); Vasan S. Sundaram, Issaquah, WA (US); David A. Bowen, Bellevue, WA (US); Shawn M. Pare, Woodinville, WA (US); Liam S. C. Pingree, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,228

(22) Filed: Jul. 9, 2014

(65) Prior Publication Data

US 2014/0322433 A1    Oct. 30, 2014

Related U.S. Application Data

(62) Division of application No. 13/898,535, filed on May 21, 2013, now Pat. No. 8,802,236, which is a division of application No. 12/409,369, filed on Mar. 23, 2009, now Pat. No. 8,465,812.

(51) Int. Cl.
| | |
|---|---|
| *C23C 16/52* | (2006.01) |
| *G01N 27/02* | (2006.01) |
| *B64C 1/14* | (2006.01) |
| *C09D 1/00* | (2006.01) |
| *C23C 16/02* | (2006.01) |
| *C23C 16/40* | (2006.01) |
| *B32B 7/02* | (2006.01) |
| *G01N 27/04* | (2006.01) |
| *B05D 1/00* | (2006.01) |
| *B05D 7/00* | (2006.01) |
| *G01N 17/00* | (2006.01) |

(52) U.S. Cl.
CPC ............... *G01N 27/02* (2013.01); *B32B 7/02* (2013.01); *B64C 1/1484* (2013.01); *C09D 1/00* (2013.01);

(Continued)

(58) Field of Classification Search
CPC .................... C23C 16/401; C23C 16/0272
USPC ............................................... 427/8
See application file for complete search history.

(56) References Cited

U.S. PATENT DOCUMENTS 5,190,807 A  *  3/1993  Kimock ............... C23C 16/006
                                                              428/216
5,228,478 A      7/1993  Kleisle
(Continued)

FOREIGN PATENT DOCUMENTS

| WO | 02072189 A2 | 9/2002 |
| WO | 03068846 A1 | 8/2003 |
| WO | 2007089550 A2 | 8/2007 |

OTHER PUBLICATIONS

European Patent Office; Extended European Search Report for European Application No. 15181297.1 dated Sep. 16, 2015, pp. 1-6.

(Continued)

*Primary Examiner* — Kelly M Gambetta

(74) *Attorney, Agent, or Firm* — Moore & Van Allen PLLC

(57) ABSTRACT

A hard, transparent coating for a substrate and associated method for coating is disclosed. The coating includes alternating layers of a soft coating and a hard coating. The coating further includes a sensor. The electrical resistivity of the sensor may be measured to determine if the coating has been degraded. The coating may further include a hydrophobic outer layer.

25 Claims, 4 Drawing Sheets

(52) U.S. Cl.
CPC ......... *C23C 16/0272* (2013.01); *C23C 16/401* (2013.01); *G01N 27/04* (2013.01); *B05D 1/62* (2013.01); *B05D 7/50* (2013.01); *B05D 2201/00* (2013.01); *G01N 17/00* (2013.01); *Y10T 428/24942* (2015.01); *Y10T 428/24983* (2015.01); *Y10T 428/31504* (2015.04)

(56) References Cited

U.S. PATENT DOCUMENTS

| | | |
|---|---|---|
| 5,344,712 A | 9/1994 | Basil et al. |
| 5,665,450 A | 9/1997 | Day et al. |
| 5,846,649 A | 12/1998 | Knapp et al. |
| 6,889,938 B1 | 5/2005 | Nordman |
| 8,465,812 B2 * | 6/2013 | Larson-Smith ....... B64C 1/1484 427/569 |
| 2004/0025568 A1 | 2/2004 | Fleischer et al. |
| 2007/0122598 A1 | 5/2007 | Coak et al. |
| 2007/0196633 A1 | 8/2007 | Coak et al. |
| 2010/0245030 A1 * | 9/2010 | Ikeda ....................... G01J 5/02 338/307 |

OTHER PUBLICATIONS

Meskinis, S., et al.; "Hydrophobic properties of the ion beam deposited DLC films containing SiOx," Thin Solid Films, 2007, pp. 7615-7618, vol. 515.

* cited by examiner

DURABLE TRANSPARENT INTELLIGENT COATINGS FOR POLYMERIC TRANSPARENCIES

CROSS-REFERENCE TO RELATED APPLICATIONS

This application is a divisional application of U.S. patent application Ser. No. 13/898,535, filed May 21, 2013, which is a divisional application of U.S. patent application Ser. No. 12/409,369 filed Mar. 23, 2009, entitled "DURABLE TRANSPARENT INTELLIGENT COATINGS FOR POLYMERIC TRANSPARENCIES," now U.S. Pat. No. 8,465,812, both of which are incorporated herein by reference in their entirety.

FIELD

This disclosure relates generally to a wear resistant coating, and more particularly, to a dual-layer transparent plasma-based durable coating for plastic substrates.

BACKGROUND

Plastics are finding increasing use in manufactured goods. For example, certain automobiles have plastic body panels, and aircraft have plastic interior paneling and exterior skin panels formed of plastics and plastic composites. While plastics offer several excellent properties including low weight, formability and low cost, plastics also have significant disadvantages. In general, plastic surfaces are not as hard or abrasion resistant as metal surfaces. Furthermore, while some plastics may be transparent, glass, which is much heavier and more expensive, remains the material of choice in certain critical applications such as automobiles and passenger aircraft windshields. Substituting polymeric materials, such as acrylic or polycarbonate materials, may lead to lighter transparencies, but may also enable re-designing the overall shape of the cockpit. Currently, stretched acrylic materials are used to fabricate aircraft passenger windows. Acrylic materials are used because of flexibility, lightness, and easy formability. However, acrylic materials are soft material and can be easily scratched. Water absorption, chemical attack, and mechanically induced scratches may lead to crazing when stress is applied, for example when the acrylic material experiences operational stresses as in an aircraft passenger window application.

Industry wide, polymer based transparencies are protected against wear and other chemical/nature induced degradation through siloxane-based coatings. At the present time, polycarbonate and other types of polymeric windows are protected by sol-gel based polysiloxane coatings. The term sol-gel or solution-gelation refers to materials undergoing a series of reactions like hydrolization and condensation. The sol-gel coatings are homogeneous mixtures of a solvent, an organosilane, an alkoxide and a catalyst that are processed to form a suitable coating. The sol-gel coatings provide high transmittance and limited durability against wear and UV induced degradation. Typically, a metal alkoxide or metal salt is hydrolyzed to form a metal hydroxide. The metal hydroxide then condenses in solution to form a hybrid organic/inorganic polymer. The ratio of organic to inorganic components in the polymer matrix is controlled to maximize the performance for a given application. For example, increasing the organic groups would improve flexibility but may compromise wear and environmentally induced durability. The sol-gel coating may include materials such as cerium or titanium to improve abrasion resistance and ultraviolet induced degradation of the coatings. A typical application process would consist of component surface cleaning, followed by the application of the coating via a flow, spray or dip process. The surface cleaning may be achieved by solvent wiping with, for example, isopropyl alcohol, or by exposing the component to oxygen plasma. The sol-gel coatings can be cured at room temperature or elevated temperatures. For example, stretched acrylics must be cured at temperatures less than 180° F.

The coatings used at the present time exhibit only a moderate durability. There is a need for a transparent, hard coating with excellent durability that would improve component lifetime. The coating should provide improved resilience against chemicals commonly encountered in product maintenance and also excellent weatherability characteristics. The coating should be both hard and flexible, so that it tolerates the flexing of the polymeric material due to operation and thermal stresses. The coating should be provided by a simple process and at a low cost.

Commercial Passenger aircraft cockpit windows are currently made of multi pane glass because of its strength and abrasion resistance. Efforts are ongoing to switch to polymeric material based flight deck windows as these materials are light, and amenable to forming desired shapes at a low cost. While plastics offer several excellent properties such as light weight, formability, and low cost, plastics also have significant short comings. In general, plastic surfaces are not as hard or abrasion resistant as glass or steel surfaces. Polymeric materials are susceptible to particle (e.g., sand)/water induced erosion and chemical crazing; protective hard coatings are needed to maintain the optical quality of the windows in use.

In addition, while a polymeric-glass laminate has less weight over an all-glass laminate, additional weight reduction could be achieved by removal of the glass facing ply if erosion and abrasion were not a problem. The polymeric-glass laminate also suffers from thermally induced stresses from the thermal expansion difference between glass and polymeric layers, which reduces service life. Furthermore, matching contours between glass and polymeric plies poses manufacturing problems, and can lead to optical and service related issues in the final part.

Duplex coating schemes have been developed that offer improved performance. These duplex coating schemes have been specifically designed for applications where good visibility is required but not critical at all times, such as aircraft passenger windows. However, the optical quality of cockpit windows is a flight critical property. With current coatings there is no non-destructive way to determine if the transparent coating is still present and protecting the polymeric substrate. Therefore, a method and coating is needed to continually insure the integrity of a protective coating.

Furthermore, there is a need for an improved wear resistant coating for polymeric transparencies and a method to insure that optical clarity is maintained. The present disclosure fulfills these needs, and further provides related advantages.

SUMMARY

The following embodiments and aspects thereof are described and illustrated in conjunction with systems and methods that are meant to be exemplary and illustrative, not limiting in scope. In various embodiments, one or more of the problems described above in the Background have been reduced or eliminated, while other embodiments are directed to other improvements.

A first embodiment of the disclosure includes a coating including at least one soft coating, at least one hard coating, and a sensor positioned between one soft coating of the at least one soft coating and one hard coating of the at least one hard coating. The at least one soft coating and the at least one hard coating have the general formula $SiO_xC_y$.

A second embodiment of the disclosure includes a method of forming a coating on a substrate including the steps of providing a substrate, depositing at least one soft coating upon the substrate, depositing at least one hard coating upon a soft coating of the at least one soft coating, and providing a sensor. The soft coating and the hard coating are deposited by a plasma deposition process. The sensor is disposed between one soft coating of the at least one soft coating and one hard coating of the at least one hard coating. The soft coating and the hard coating having the general formula $SiO_xC_y$.

A third embodiment of the disclosure includes a composite article including a substrate and a coating deposited upon the substrate. The coating includes a soft coating disposed upon the substrate, a hard coating disposed upon the soft coating, and a sensor disposed upon the hard coating. The soft coating and the hard coating are formed by a plasma deposition process, the soft coating and the hard coating having the general formula $SiO_xC_y$.

A fourth embodiment of the disclosure includes a method of monitoring the condition of a coated substrate including the steps of providing a coated substrate comprising a substrate and a coating formed upon the substrate, and monitoring the electrical conductivity of sensor embedded within the coating. In this method, a change in the electrical conductivity of the sensor indicates a deterioration of the coating.

One advantage of the present disclosure is to provide an intelligent, transparent, hard coating with excellent durability.

Another advantage of the present disclosure is to provide an intelligent, transparent hard coating that improves component lifetime.

Another advantage of the present disclosure is to provide an intelligent, transparent, hard coating that is both hard and flexible.

Another advantage of the present disclosure is to provide a transparent, hard coating that provides improved resistance against chemicals commonly encountered in product maintenance.

Another advantage of the present disclosure is to provide a transparent, hard coating providing excellent weatherability characteristics.

Another advantage of the present disclosure is to provide a process for applying an intelligent, transparent, hard coating.

Another advantage of the present disclosure is to provide an intelligent, transparent hard coating at temperatures compatible with the substrates or without damaging the substrate or degrading its physical properties.

Another advantage of the present disclosure is to provide an intelligent, transparent hard coating that can be substantially seamlessly varied within the coating thickness.

Another advantage of the present disclosure is to provide an intelligent, transparent, hard coating that includes a nondestructive system for indicating when the coating needs replaced.

Another advantage of the present disclosure is to provide an intelligent, transparent, hard coating that includes a sensor for indicating when the coating has been exposed to a predetermined environmental condition.

Another advantage of the present disclosure is to provide an intelligent, transparent, hard coating that includes a sensor to indicate if the coating is present and protecting an underlying substrate.

Further aspects of the method and apparatus are disclosed herein. Other features and advantages of the present disclosure will be apparent from the following more detailed description of the preferred embodiment, taken in conjunction with the accompanying drawings that illustrate, by way of example, the principles of the invention. The features, functions, and advantages of the present disclosure can be achieved independently in various embodiments of the present disclosure or may be combined in yet other embodiments.

DETAILED DESCRIPTION OF THE INVENTION

The present disclosure now will be described more fully hereinafter with reference to the accompanying drawing, in which a preferred embodiment of the disclosure is shown. This disclosure may, however, be embodied in many different forms and should not be construed as limited to the embodiments set forth herein; rather, these embodiments are provided so that this disclosure will be thorough and complete and will fully convey the scope of the disclosure to those skilled in the art. All composition percents are given as weight percents, unless otherwise specified.

Figure 1:
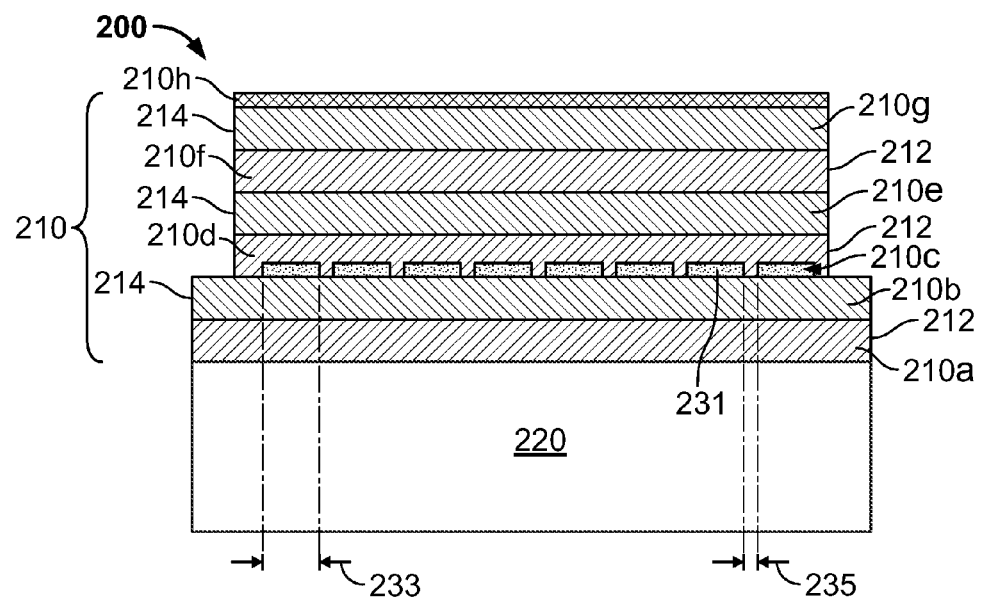
FIG. 1 illustrates an exemplary embodiment of a coated substrate according to the invention.

FIG. 1 illustrates an embodiment of an exemplary coated article 200 according to the disclosure. The coated article 200 includes a coating 210 and a substrate 220. The coated article 200 may be an aircraft window, aircraft cockpit canopy, or other coated transparent substrate. For example, the coated article 200 may be selected from a group including, but not limited to an acrylic aircraft window, an airplane cockpit, an airplane navigation light lens, and a fiberglass-epoxy radome. Additionally, the coated article 200 need not be limited to the aircraft industry. For example, the coated article 200 may further be selected from a group including, but not limited to consumer electronics such as polycarbonate cases for consumer electronics, cell phone touch screens, and automotive applications such as automobile parts, panels, windows and windshields, as well as other industry applications in which transparent articles may be exposed to wear and damage.

The substrate 220 may be a metal, a rigid polymer material such as an acrylic, polycarbonate or plastic, a fiber reinforced polymer matrix, an amorphous material such as glass, or other similar material. The substrate 220 may be a hard, soft, flexible or rigid material. The coating 210 benefits any substrate 220 where the coating 210 is harder than the substrate 220. In one embodiment, the substrate 220 may be an aircraft passenger window formed of acrylic or other similar polymeric material. For example, the coating 210 may be applied to stretched acrylic substrate, such as a stretched acrylic aircraft window, to improve crack growth resistance. U.S. Patent Publication No. 2007/0122598A1, published May 31, 2007, and U.S. patent application Ser. No. 12/137,390, filed Jun. 11, 2008, disclose duplex coating schemes that include soft and hard coating layers, the disclosures both of which are incorporated by reference herein in their entireties.

As can be further seen in FIG. 1, the coating 210 includes alternating layers of a soft coating 212 and a hard coating 214. The soft coating 212 and hard coating 214 provide protection for substrate 220. Each soft coating 212 and hard coating 214 may have a thickness of from about less than 1 µm to about 20 µm thick. In another embodiment, each soft coating 212 and hard coating 214 may have a thickness of from about 1 µm to about 10 µm.

The coating 210 also includes a sensor 210c disposed, positioned or otherwise embedded in the coating 210. The sensor 210c is an indicator as to the condition of the coating 210. The sensor 210c may be referred to as an active health monitoring layer or an active health monitoring sensor. The coating 210 further includes an optional outer layer 210h. The outer layer 210h may be a hydrophobic layer or a self-cleaning layer. In another embodiment, the outer layer 210h may be omitted.

In the exemplary embodiment shown in FIG. 1, the coating 210 includes six alternating layers of soft coating 212 and hard coating 214. However, in another embodiment, any number of alternating layers of soft coating 212 and hard coating 214 may be used, provided the coating layer adjacent the substrate 220 is a soft coating 212 and the outermost soft coating or hard coating is a hard coating 214. As defined herein, the term soft is defined as having a hardness factor less than that of an adjacent outer hard coating layer. The hardness factor may be selected from the group including, but not limited to known hardness factors including scratch hardness, indentation hardness, rebound/dynamic hardness, weatherability, and wear.

The soft coating 212 has greater adhesion and flexibility characteristics relative to the hard coating 214. The greater adhesion and flexibility of the soft coating 212 improves the adhesion of the coating 210 to the substrate 220. The soft coating 212 provides a bonding layer and thus is deposited prior to depositing hard coating 214. Soft coating 212 need not be thick to provide the adhesion benefit to the hard coating 214. In one embodiment, the soft coating 212 may have a thickness of between about 1.5 µm and 7 µm. For example, the soft coating 212 may have a thickness of about 2 µm, 3 µm, or 4 µm. The thickness of the soft coating 212 is sufficient to ensure the adhesion of hard coating 214 to substrate 220.

In one embodiment, the soft coating 212 has a general composition of $SiO_xC_y$ having about 30% to about 35% Si, about 30% to about 35% C, and about 30% to about 35% O.

In one embodiment, the soft coating 212 has a hardness of about 0.2 GPa to about 1.5 GPa. Within this disclosure, all composition percentages are provided as weight percentages.

As discussed above, the hard coating 214 has greater hardness, wear, and weatherability characteristics relative to the soft coating 212. The greater hardness, wear, and weatherability characteristics improve the resistance of the coating 210 against mechanical scratching, chemical attack, and environmental degradation. In one embodiment, the hard coating 214 may have a thickness of between about 1.5 µm and 7 µm. For example, the hard coating 214 may have a thickness of about 2 µm, 3 µm, or 4 µm. The thickness of the hard coating 214 is sufficient to provide a desired durability to the coating 210.

In one embodiment, the hard coating 214 has a general composition of $SiO_xC_y$ having about 30% to about 35% Si, about 25% to about 30% C, and about 40% to about 45% O. In one embodiment, the hard coating 204 has a hardness of about 1.5 GPa to about 10.0 GPa.

As shown in FIG. 1, the thickness of each layer of the soft coatings 212 and hard coatings 214 are approximately equal. In yet another embodiment, each layer of the soft coating 212 and/or the hard coating 214 may vary in thickness, or in other words, have unequal thickness. In still another embodiment, the coating 200 may include one or more soft coatings 212 and one or more hard coatings 214. For example, different soft coatings 212 and/or different hard coatings 214 may be used that vary in composition, thickness, and/or hardness.

The coating 210 improves resistance of the substrate 220 to surface effects. In one embodiment, the abrasion resistance of the coating 210, as measured by the percent change in haze as measured in a Taber wear Test (ASTM D-1044-08), is greater than two orders of magnitude better than that for a polysiloxane coated polycarbonate substrate. In one exemplary embodiment, after 1,000 taber cycles, an exemplary coated article 200 according to the disclosure had a change in haze of about 2.8% as compared to a change in haze of about 25% for a polysiloxane coated substrate. In one embodiment, the erosion resistance of the coating 210, as measured by percent change in haze as measured in a Falling Sand Test (ASTM D 968-05), is greater than a factor of three better than the erosion resistance of glass. In addition, the optical properties, including light transmittance in the visible region, clarity and haze, of a substrate 220 with a coating 210 disposed thereupon are approximately equal to the same properties of a substrate 220 with a single polysiloxane coating.

In the exemplary embodiment shown in FIG. 1, the coating 210 includes eight consecutive layers numbered 210a, 210b, 210c, 210d, 210e, 210f, 210g, and 210h, respectively. The first layer 210a and the second layer 210b are approximately 5 microns thick, and are composed of $Si_xO_yC_z$ having differing mechanical properties. The first layer 210a is relatively soft to improve the coating adhesion and flexibility, having a hardness of between about 0.5 GPa and about 1.5 GPa, and a modulus of between about 5 GPa and about 10 GPa. The second layer 210b is slightly hard with a hardness of between about 1.5 GPa and about 6 GPa, and a modulus of between about 10 GPa and about 15 GPa.

The third layer 210c is a sensor. The sensor 210c is formed of a conductive material. The sensor 210c is positioned, disposed or otherwise embedded between the second layer 210b and the fourth layer 210d. In this exemplary embodiment, the sensor 210c is formed of conductive strips 231. The conductive strips 231 may be a conductive metal, metal oxide, or composition. In one embodiment, the conductive strips 231 are indium tin oxide (ITO) strips. In one embodiment, the conductive strips 231 have a width 233 of between about 1 mil and about 5 inches. In another embodiment, the conductive strips 231 have a width between about 1 mil and about 2 inches. In yet another embodiment, the conductive strips 231 may have a width 233 of between about 0.25 inch and about 1 inch. In another embodiment, the conductive strips 231 have a width 233 selected to provide a desired coverage in the coating 210. In one embodiment, the conductive strips 231 are separated by a separation distance 235 of between about 1 mil to about 5 inches. In another embodiment, the separation distance 235 is between about 1 mil and about 0.25 inches. In another embodiment, the separation distance 235 is selected to provide a desired coverage in the coating 210. In one embodiment, the conductive strips 231 may have a thickness of between about 10 nm to about 1 µm. In another embodiment, the thickness of between about 40 nm to about 100 nm.

In this exemplary embodiment, the sensor 210c is above and adjacent the second layer 210b, or in other words, is above a soft layer 212 and hard layer 214 pair. In another embodiment, the sensor 210c is above a soft layer 212. In yet another embodiment, the sensor 210c is above at least one soft layer 212 and at least one hard layer 214 pair.

In another embodiment, sensor 210c may be formed of, for example, but not limited to Cu, ITO, ZnO, Al doped ZnO, doped metallic oxides, conductive polymers such as PEDOT:PSS, polythiophenes, pentacene, [6,6]-phenyl-C61-butryic acid methyl ester or other fullerene derivatives. The sensor 210c can be deposited using plasma deposition, chemical vapor deposition, thermal evaporation, sputtering, ink jet or screen printing, or other solution processing techniques.

Figure 1A:
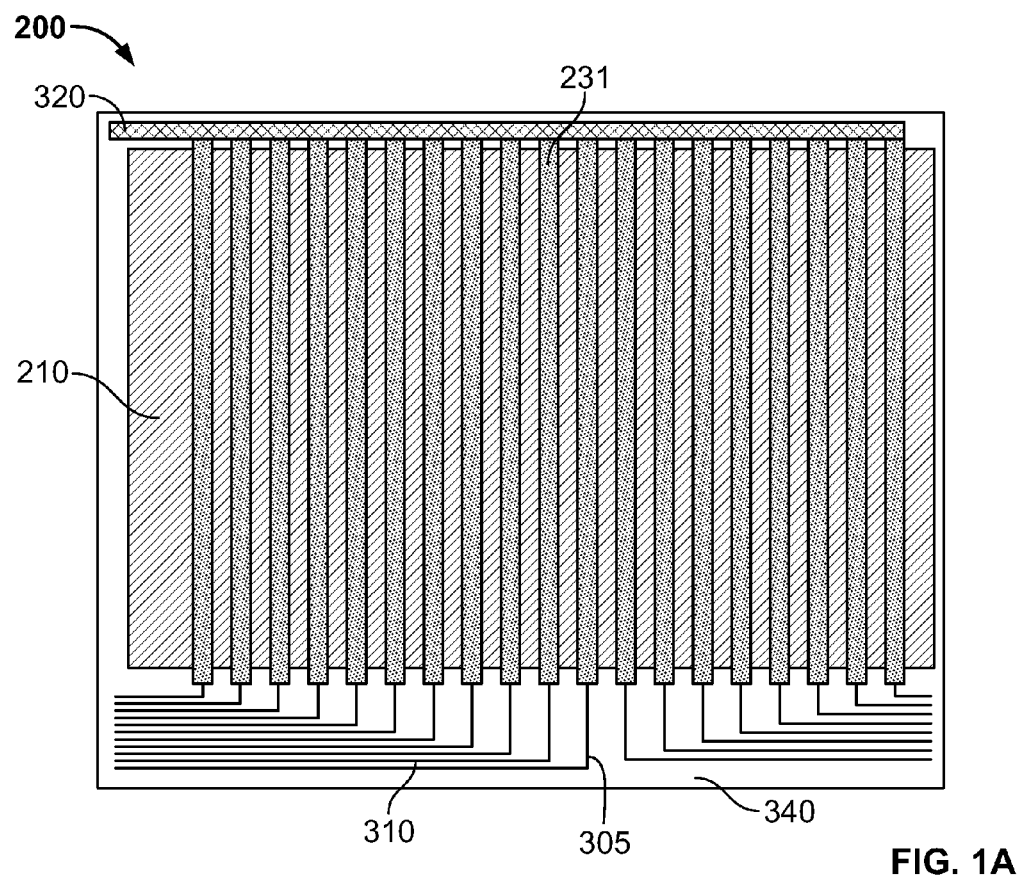
FIG. 1A is a top view of the coated substrate of FIG. 1.
Figure 1B:
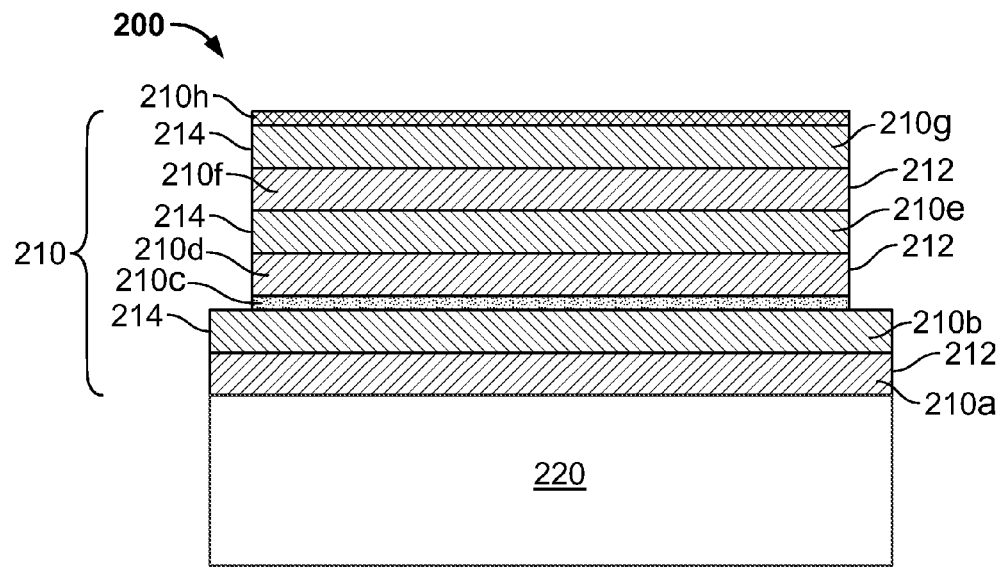
FIG. 1B illustrates another exemplary embodiment of a coated substrate according to the disclosure.

FIG. 1A shows a top view of the coated substrate 200. As can be seen in FIG. 1B, the coated substrate 200 further includes conductive leads 305. The conductive leads 305 are attached to the conductive strips 231. The conductive leads 305 are positioned upon a bus bar 310, and electrically connected to a monitoring system (not shown). The monitoring system may be a resistivity meter or other device to monitor the resistivity and/or reactance of the conductive strips 231.

In one embodiment, the condition of the coating 210 may be monitored by measuring the resistance of the sensor 210c and determining if a change occurs. The sensor 210c may be monitored at predetermined times or continuously. A degradation to the coating 210, such as an abrasion to the coating 210, that effected the resistance to any one of the conductive strips 231, would be observed as a change to the resistance of the sensor 210c. In another embodiment, a chemical reaction with the coating 210 that effected the resistance to any one of the conductive strips 231 would be observed as a change to the resistance of the sensor 210c.

FIG. 1B illustrates another embodiment of an exemplary coated article 200 according to the disclosure. The coated article 200 includes a coating 210 and a substrate 220. In this exemplary embodiment, the sensor 210c is a conductive layer or film positioned, disposed or located between the second layer 210b and the fourth layer 210d. In another embodiment, the sensor 210c may be positioned between any soft layer 212 and hard layer 214, so as to provide an indicator at any level of penetration through the coating 210. In one embodiment, the sensor 210c is positioned upon and above a hard layer 214.

The sensor 210c is a conductive material, such as ITO, described above. In one embodiment, the sensor 210c may have a thickness of between about 10 nm to about 5 µm. In another embodiment, the sensor 210c may have a thickness of between about 10 nm and about 500 nm. In yet another embodiment, the sensor 210c may have a thickness of about 100 nm.

In this exemplary embodiment, the resistance across the sensor 210c can be measured between multiple locations, for example, at multiple perimeter locations (not shown, but analogous to FIG. 1A), so that deviations between the measured resistances indicates a degradation to the coating 210.

Figure 1C:
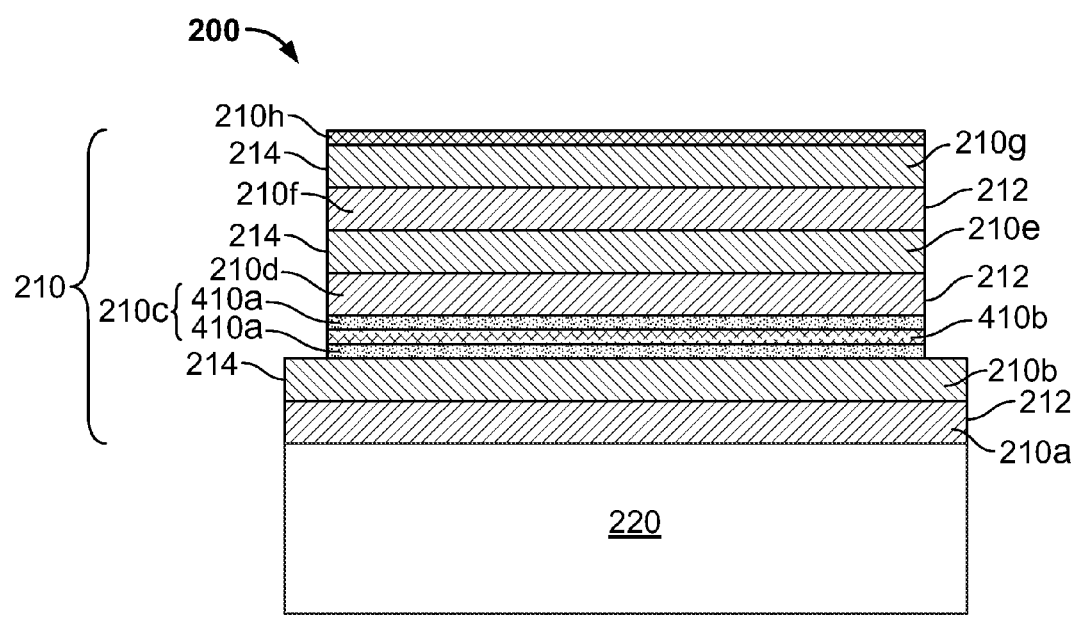
FIG. 1C illustrates yet another exemplary embodiment of a coated substrate according to the disclosure.

FIG. 1C illustrates yet another exemplary embodiment of a coated article 200 according to the disclosure. The coated article 200 includes a coating 210 and a substrate 220. In this exemplary embodiment, the sensor 210c includes two conductive layers or films 410a and a dielectric layer 410b disposed therebetween. The sensor 210c is positioned, disposed or located between the second layer 210b and the fourth layer 210d. In another embodiment, the sensor 210c may be positioned between any soft layer 212 and hard layer 214, so as to provide an indicator at any level of penetration through the coating 210. In one embodiment, the sensor 210c is positioned upon and above a hard layer 214.

The conductive layers 410a may are the same or similar to the sensor 210c in the embodiment as described in FIG. 1B. The dielectric layer 410b may be a siloxane layer or other transparent dielectric layer. The sensor 210c is a conductive material, such as ITO, described above. In one embodiment, the dielectric layer 410b may have a thickness of between about 10 nm to about 2 µm. In another embodiment, the dielectric layer 410b may have a thickness of between about 250 nm and about 2 µm. In yet another embodiment, the dielectric layer 410b may have a thickness of about 1.5 µm. In this embodiment, the resistance and/or reactance between the conductive layers 410a is measured, and measured changes in the resistance and/or reactance would indicate damage to the coating 210, as described above.

In a method of forming the coated substrate 200 according to the disclosure, a plasma based deposition technique can be used to deposit transparent silicon oxycarbide layers between about less than 1 µm to about 10 µm to form the alternating soft and hard, flexible multi-layers. In this scheme, process parameters, for example, the oxygen to silicon precursor ratio, would determine coating characteristics such as hardness and modulus.

In one embodiment, the coated article 200 may be formed masking the substrate 220 during production so that the coating layers are not present on an outer perimeter strip 340 (FIG. 1A). In one embodiment, the outer perimeter strip 340 has a width of between about 0.25 to about 1.0 inches. In yet another embodiment, the outer perimeter strip has a width of about 0.5 inches. A busbar 310 (FIG. 1A) may be installed to monitor the resistance of each conductive strip 231.

In another exemplary embodiment, a coated article 200 and a method of forming the coated article 200 is disclosed that includes a plasma based deposition technique to deposit transparent silicon oxycarbide nano-layers to form alternating soft and hard, flexible multi-layers. In this scheme, process parameters, for example, the oxygen to silicon precursor ratio, would determine coating characteristics such as hardness and modulus. The layer thicknesses will be in the nanometer range so that nanostructure induced, for example Hall-Pitch effect, mechanical strength will be in effect. The alternating nano multilayer design creates more interfaces which allows for any advancing crack to be deflected, thereby dissipating energy and improving toughness.

In another embodiment, the coating 210 is formed by depositing alternating layers of soft coating 212 and hard coating 214 having differing $SiO_xC_y$ compositions. The coating 210 is further formed by depositing the sensor 210c between a soft coating 212 and a hard coating 214 and by depositing a hydrophobic layer 210h on the outermost hard coating 214. The coating 210 is formed by using either a mixture of sol-gel based soft coating and plasma coating, or a plasma based deposition process alone, where the hardness of the coating layers is controlled via processing parameters during deposition. The coating 210 may be formed in a single step continuous process or may be formed by a multiple step discontinuous process. In some embodiments, a substantially seamless material transition exits between the alternating layers of the soft coating 212 and the hard coating 214, which results from the use of the plasma deposition process to deposit both layers. In one embodiment, the coating 210 is formed in a single coating process without removing the substrate 220 from the process chamber. In yet another embodiment, the substrate 220 is not removed from the process chamber and input parameters such as chemical gas flow rates, are varied during the coating process. By controlling and adjusting the deposition process parameters, individual layer characteristics including composition, layer thickness, hardness and modulus may be controlled and individually selected for each deposited layer. Furthermore, deposition parameters such as bias voltage, pressure, temperature and flow rate can be controlled and adjusted to influence the microstructure of the coating and its relative hardness or softness. Thus, two coatings with the same chemical composition may have different coating densities and/or stoichiometries, thus having different hardness and modulus characteristics.

The plasma based deposition process of the current invention uses a plasma-enhanced chemical vapor deposition (PE-CVD) that uses the energy of plasma electrons to disassociate process gases. The plasma source includes a radio frequency or microwave power source and an appropriate applicator. For example, a plasma reactor using microwave power at 2.45 GHz may be used to dissociate and ionize the process gasses. The layers can be deposited at low substrate temperatures of between about 20° C. to about 30° C. The PE-CVC conditions, such as gas flow, deposition pressure, plasma power, plasma pulse frequency and duty cycles may be adjusted to produce a hard, transparent coating in accordance with known plasma deposition principles.

The process further employs the principal of Electron Cyclotron Resonance (ECR), in which a static magnetic field is applied along the direction of microwave propagation. Resonance occurs when the microwave radian frequency ω is equal to the cyclotron frequency $\omega_c=qB/m_e$, where q is the electronic charge, B is the magnetic field strength, and $m_e$ is the electron mass. If f=2.45 GHz, the resonance field value is 875 Gauss. At resonance, the electrons gyrate in synchronism with the oscillating microwave field. The plasma electrons are thus accelerated by the microwave field.

The process gas used in this deposition process is oxygen used in combination with an organosilicon precursor gas. For example, the precursor gas may be any one of octamethycyclotetrasiloxane ($C_8H_{24}O_4Si_4$)), also know as OMCTS, hexamethyldisiloxane ($Si_2C_6H_{18}O$), tetramethylcyclotetrasiloxane ($SI_4C_4H_{16}O_4$), and octamethylcyclotetrasiloxane (($SiO)_4(CH_3)_8$). In one embodiment, OMCTS is used as the precursor gas. The OMCTS vapor pressure at room temperature is approximately one Torr, which greatly facilitates vapor introduction into the process chamber. Additionally, the Hazardous Materials Identification System (HMIS®) hazard rating for OMCTS is 1-2-0, which means that OMCTS is about as safe as a typical house paint. In another embodiment, combinations of different precursor gases may be used.

To deposit the alternating layers of $SiO_xC_y$, the OMCTS can be heated to about 70° C. to increase vapor pressure of the OMCTS. The vapor is then metered into the process chamber by a heated mass flow controller. The vapor is introduced just above the substrate through four ports equally spaced around the chamber, while oxygen $O_2$ is injected through four ports located under the input microwave window. In one deposition chamber geometry, the ratio of OMCTS to $O_2$ (OMCTS/$O_2$) is between about 40 to about 60 to form a soft layer and is between about 15 to about 35 to form a hard layer. In one embodiment, the substrate is neither heated nor cooled by external systems and/or methods, and is at ambient temperature at the start of the deposition process. The substrate temperature may increase as a result of the coating deposition. In another embodiment, the substrate temperature is less than about 65° C. during the deposition.

In one embodiment, referred to as Example 1, a coating 100 was formed by using an OMCTS/$O_2$ of between about 45% to about 55% to form a soft coating 212 having a composition of about 31% to about 33% Si, about 33% to about 35% C, and about 31% to about 33% O, and having a hardness of about 1.5 GPa to about 1.65 GPa. A hard coating 214 was then formed upon the soft coating 212 by using a OMCTS/$O_2$ of between about 20% to about 30% having a composition of about 31% to about 33% Si, about 25% to about 27% C, and about 40% to about 42% O, and having a hardness of about 1.5 GPa to about 2.0 GPa.

In one embodiment, sensor 210c is deposited with the use of a shadow mask in a thermal deposition, CVD chamber, or sputter chamber. The mask shadows the region between the separation distance 235 (FIG. 1). In another embodiment, the sensor is printed onto the hard layer (210b) via direct contact printing or a screen printing process. In another embodiment, sensor 210c is a continuous sheet formed via one of the aforementioned deposition processes. In another embodiment shown in FIG. 1C, sensor 210c includes conductive layers 410a formed by a printed or deposited method with an insulating layer 410b deposited therebetween.

In one embodiment, marker layer 210h is applied by spreading the aqueous solution containing the constituent composition with an applicator. This applicator can be a paint brush, cotton swab, clean rag/gauze, or the solution can be sprayed on. Some hydrophobic layers may require a low temperature cure after deposition is complete.

In one embodiment, substrate 220, prior to being loaded into a plasma deposition chamber for the application of the coating 210, may be first chemically cleaned to remove contaminants such as hydrocarbons and other undesirable materials. The cleaning process may be accomplished using, for example, ultrasonic cleaning in solvents or aqueous detergents. Once the desired vacuum conditions are obtained, substrate 220 may be sputter cleaned using inert ions and/or oxygen ions. Once the cleaning step is complete, the hard coating application can commence.

Figure 2:
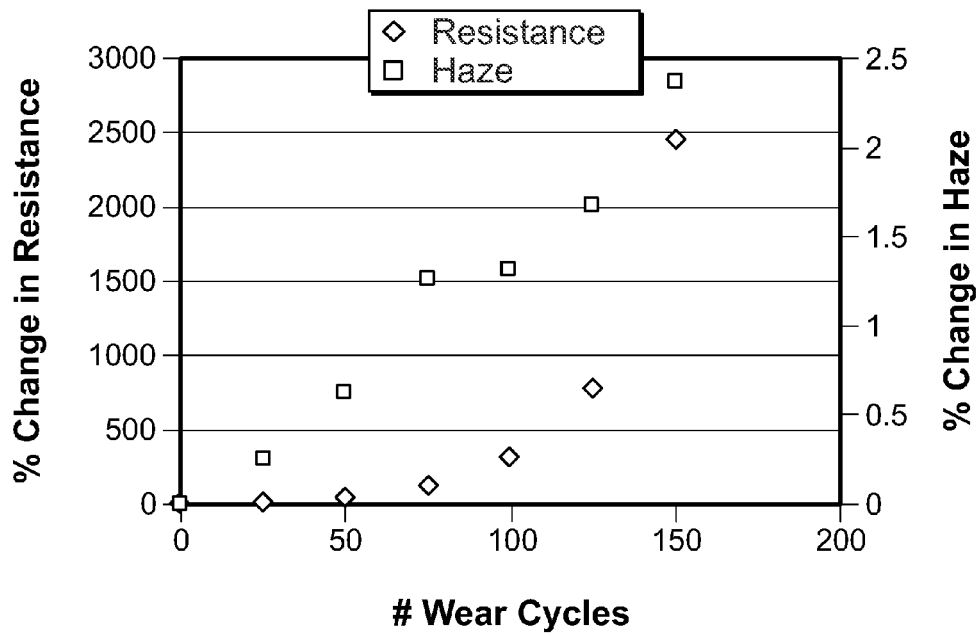
FIG. 2 is a graph showing the results of a test determining optical haze and resistance of the marker band as a function of Taber wear cycle for an exemplary coating according to the disclosure.

One set of samples was prepared in which an ITO marker layer of thickness 100 nm and width of 0.125 inches was deposited on an acrylic sample with a hard transparent coating. Coated substrates were tested for wear in accordance with the procedure described in ASTM D-1044-90, "Standard Test Method for Resistance of Transparent Plastics to Surface Abrasion". This test consists of two CS-10 wheels to which a 500 g load is applied. The wheels abrade the substrate surface as it rotates on a table. In the present tests, both the optical haze and the resistance of the ITO band were monitored as a function of Taber wear cycle. FIG. 2 shows a graph of the test results.

As can be seen in FIG. 2, the percent change in the electrical resistance of the ITO band and the optical haze through the ITO band as a function of Taber wear cycle is plotted. The graph shown in FIG. 2 shows that as the sensor is starting to wear, both optical haze and the electrical resistance increase, which establishes that the resistance can be externally monitored to gage the ability of the coating to protect the underlying polymeric substrate.

Figure 3:
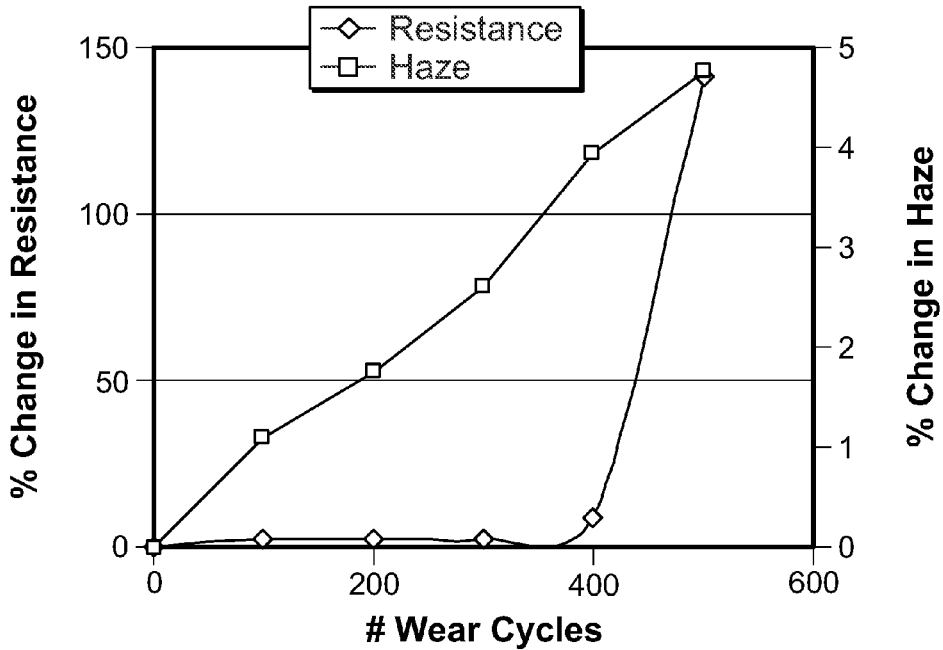
FIG. 3 is a graph showing the results of a test determining optical haze and resistance of the marker band as a function of Taber wear cycle for another exemplary coating according to the disclosure.

In another test, a sensor in the form of an ITO layer having a thickness 100 nm and width of 0.125 inches was deposited on an acrylic coupon. A polysiloxane hard coating was then applied on top of this ITO layer. The coupon was wear tested in accordance to the ASTM D-1044-90 test protocol. The graph shown in FIG. 3 plots the percent change in the ITO layer resistance and the optical haze as a function of the Taber wear cycle. As the polysiloxane hard coating starts to wear down, as discerned by the haze change, the underlying sensor starts wearing, and the resistance of the sensor starts to increase. As above, the sensor resistance change can be monitored to determine the condition the coating.

In another test, a sensor formed of a 100 A thick and one inch wide copper band was applied on an acrylic substrate coupon. A polysiloxane hard coating was applied on top of the copper band. The coupon was wear tested according to the ASTM D-1044-90 test protocol, and a graph of the results is shown in FIG. 4.

Figure 4:
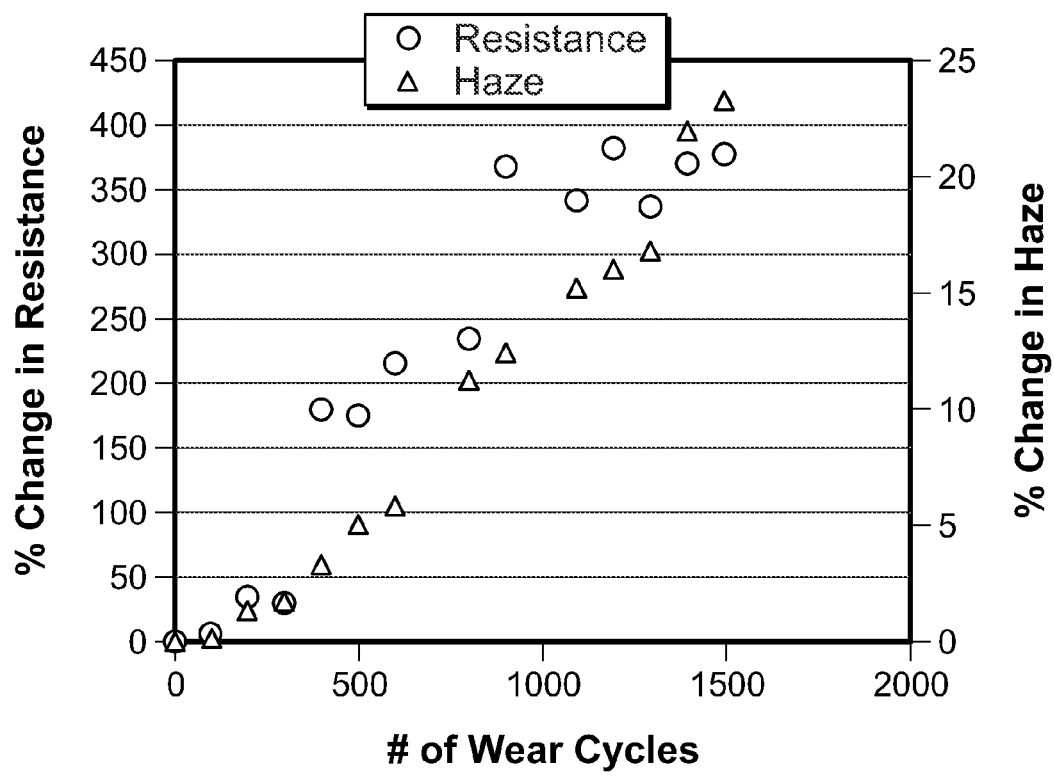
FIG. 4 is a graph showing the results of a test determining optical haze and resistance of the marker band as a function of Taber wear cycle for another exemplary coating according to the disclosure.

FIG. 4 shows the change in the sensor resistance and optical haze as a function of the Taber wear cycle. As the polysiloxane hard coating starts to wear down, as discerned by the haze change, the underlying sensor starts wearing and the resistance of the sensor starts to increase. Again, as discussed above, the change in the sensor resistance can be used to monitor the condition of the top hard coating.

The higher refractive index of the sensor, when compared to the substrate, reduces the optical transmission through the coated article. However, the presence of additional hard layers on top of the sensor can help restore the transmission as the coatings have a lower refractive index, thus creating less reflection at both interfaces. For sensors formed of metallic conductive layers, the high coefficient of absorption across visible wavelengths renders transmission through the stack highly dependent upon the thickness of said coating. In the test shown above the thickness of a copper layer was 100 A as a proof of concept, albeit the transmission through this sensor was lower than desirable for the application. In actual application, thin metallic layers (10-50 A thick copper or gold) or an ITO layer can be used to minimize these effects.

One unique feature of this disclosure is that it can be applied in a single step using a plasma based deposition process. By tuning the process parameter, the present scheme allows manipulation of individual layer characteristics such as layer thickness, hardness and modulus. The ability to change these coating characteristics enables the applicability of the same system to process products for different applications, such as windows for aircraft or cell phone screens, where the requirements can be vastly different. For example, aircraft window coatings need to be hard and flexible, whereas in such applications as consumer electronics the coatings should be resistant to wear and exposure to common consumables such as carbonated beverages. From a manufacturing point of view, both the coating application cost and product thru-put are increased.

This disclosure describes an extremely durable transparent coating that can be monitored to ensure coating effectiveness. In one embodiment, the coating may be constantly monitored. In another embodiment, the coating may be periodically monitored. In one embodiment, the electrical resistance of the marker layer is monitored. In another embodiment, the electrical resistance of one or more of the conductive fingers is measured. A change in resistance indicates the outer layers of the coating are no long intact and the coating or window should be repaired or replaced. This invention allows for the use of protective coatings in flight critical applications such as cockpit windows Though this disclosure is aimed at transparent substrates, such as windows, any critical application where monitoring of the effectiveness of a hard protective coating is desired or required to protect a substrate is feasible. In one embodiment, degradation of the marker layer provides a warning that the coating needs repair before damage to the substrate occurs. Application of this coating concept to highly abrasive surfaces such as leading edges, wear surfaces, or joints could be applied where protection of the substrate is needed and it is desired to have a means to warn of impending damage to the substrate before it occurs. This would allow for the repair of the part or coating before any damage to the substrate occurs.

While the disclosure has been described with reference to a few preferred embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. It is therefore intended that the following appended claims and claims hereafter introduced are interpreted to include all such modifications, permutations, additions, and sub-combinations as are within their true spirit and scope.

The invention claimed is:

1. A method of monitoring the condition of a coated substrate, comprising:
    monitoring the electrical conductivity of a sensor embedded within two or more $SiO_xC_y$ coatings formed on a substrate; wherein the values x and y are nonzero; and
    providing an indication of a change in the electrical conductivity of the sensor.

2. The method of claim 1 herein the electrical conductivity of the sensor is monitored continuously.

3. The method of claim 1 wherein the electrical conductivity of the sensor is monitored at a predetermined time.

4. The method of claim 1 wherein the two or more coatings are deposited $SiO_xC_y$.

5. The method of claim 4 wherein the coating comprises at least one soft coating and at least one hard coating.

6. The method of claim 5 wherein the at least one soft coating and the at least one hard coating have the general formula $SiO_xC_y$, wherein the soft coating composition is, in weight percent, 30-35% Si, 30-35% C and 30-35% O, and wherein the hard coating composition is, in weight percent, 30-35% Si, 25-30% C and 40-45% O.

7. The method of claim 6 wherein the soft coating has a hardness in the range of 0.2-1.5 GPa and wherein the hard coating has a hardness in the range of 1.5-10 GPa provided that the hard coating has a hardness greater than the soft coating.

8. A method of monitoring the condition of a coated substrate, comprising:
   forming a coating upon a substrate, the coating comprising:
      at least one soft coating;
      at least one hard coating; and
   embedding a sensor positioned between one soft coating of the at least one soft coating and one hard coating of the at least one hard coating;
   wherein the at least one soft coating and the at least one hard coating have the general formula SiOxCy, wherein the values x and y are nonzero; and wherein the soft coating composition is, in weight percent, 30-35% Si, 30-35% C and 30-35% O;
   monitoring the electrical conductivity of sensor embedded within the coating, wherein a change in the electrical conductivity of the sensor indicates a deterioration of the coating.

9. The method of claim 8 wherein the soft coating has a hardness in the range of 0.2-1.5 GPa.

10. The method of claim 9 wherein the hard coating composition is, in weight percent, 30-35% Si, 25-30% C and 40-45% O and the hard coating has a hardness in the range of 1.5-10 GPa provided that the hard coating has a hardness greater than the soft coating.

11. The method of claim 8, further comprising multiple alternating layers of the soft coating and the hard coating.

12. The method of claim 8, further comprising a hydrophobic layer deposited upon an outermost hard coating.

13. The method of claim 8, wherein the sensor comprises a conductive material.

14. The method of claim 8, wherein the sensor comprises a plurality of conductive strips.

15. The method of claim 8, wherein the sensor comprises a conductive film or sheet.

16. The method of claim 8, wherein the sensor comprises a first conductive film, a second conductive film, and a dielectric layer positioned between the first conductive film and the second conductive film.

17. The method of claim 8 further comprising the step of measuring a resistance using a device electrically connected to the sensor.

18. The method of claim 8 wherein the substrate is transparent.

19. A method comprising:
   positioning a sensor on at least one soft coating of a substrate, the sensor configured to monitor a change of electrical conductivity;
   depositing at least one hard coating on the sensor and on at least a portion of the at least one soft coating, whereby the sensor is embedded within the coating;
   wherein the at least one soft coating and the at least one hard coating have the general formula SiOxCy, wherein x and y are nonzero; and wherein the soft coating composition is, in weight percent, 30-35% Si, 30-35% C and 30-35% O.

20. The method of claim 19 wherein the soft coating has a hardness in the range of 0.2-1.5 GPa.

21. The method of claim 19 wherein the hard coating composition is, in weight percent, 30-35% Si, 25-30% C and 40-45% O.

22. The method of claim 19 wherein the hard coating has a hardness in the range of 1.5-10 GPa provided that the hard coating has a hardness greater than the soft coating.

23. The method of claim 19, further comprising alternating multiple layers of the soft coating and the hard coating.

24. The method of claim 19, further comprising depositing a hydrophobic layer on the hard coating.

25. The method of claim 19, wherein the sensor comprises a conductive material.

\* \* \* \* \*